United States Patent
Campbell et al.

(12) 
(10) Patent No.: US 6,271,232 B1
(45) Date of Patent: *Aug. 7, 2001

(54) COLLAGENASE-1 AND STROMELYSIN-1 INHIBITORS, PHARMACEUTICAL COMPOSITIONS COMPRISING SAME AND METHODS OF THEIR USE

(75) Inventors: David Campbell, San Mateo; Gary C. Look; Anna Katrin Szardenings, both of Santa Clara; Dinesh V. Patel, Fremont, all of CA (US)

(73) Assignee: Affymax Technologies, N.V., Greenford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/350,878

(22) Filed: Jul. 9, 1999

Related U.S. Application Data

(63) Continuation of application No. 08/665,603, filed on Jun. 18, 1996, now Pat. No. 5,932,579.

(51) Int. Cl.[7] ..................... A61K 31/495; C07D 241/36; C07D 241/04; C07D 237/00
(52) U.S. Cl. ........................ 514/249; 514/255; 544/231; 544/349; 544/385
(58) Field of Search .................................. 544/231, 349, 544/385; 514/249, 255

(56) References Cited

U.S. PATENT DOCUMENTS

| | | | |
|---|---|---|---|
| 4,371,466 | 2/1983 | McGregor | 260/112.5 |
| 4,595,700 | 6/1986 | Donald et al. | 514/616 |
| 4,599,361 | 7/1986 | Dickens et al. | 514/575 |
| 4,609,667 | 9/1986 | Clark et al. | 514/367 |
| 4,806,538 | 2/1989 | Shimazaki et al. | 514/253 |
| 4,940,709 | 7/1990 | Shimazaki et al. | 514/237.8 |
| 5,109,000 | 4/1992 | Markwell et al. | 514/445 |
| 5,240,958 | 8/1993 | Campion et al. | 514/238.2 |
| 5,304,604 | 4/1994 | Davidson et al. | 514/575 |
| 5,310,763 | 5/1994 | Campion et al. | 514/389 |
| 5,712,300 | 1/1998 | Jacobsen | 514/389 |

FOREIGN PATENT DOCUMENTS

| | | | |
|---|---|---|---|
| 0 181 152 | 5/1986 | (EP) | C07D/403/06 |
| 0 185 380 | 6/1986 | (EP) | C07C/149/23 |
| 0 236 872 | 9/1987 | (EP) | C07K/5/06 |
| 0 273 689 | 7/1988 | (EP) | C07C/149/23 |
| 0 322 184 | 6/1989 | (EP) | C07C/149/23 |
| 0 423 943 | 4/1991 | (EP) | A61K/31/405 |
| WO 88/06890 | 9/1988 | (WO) | A61K/37/02 |
| WO 94/07481 | 4/1994 | (WO) | A61K/31/16 |
| WO 96/00391 | 1/1996 | (WO) | G01N/33/53 |
| WO 97/48685 | 12/1997 | (WO) | C07D/241/08 |

OTHER PUBLICATIONS

Baililien et al. (1986), "Teratogenic effect of acetohydroxamic acid in clinically normal Beagles," Am. J. Vet. Res. 74:2604–2611.

Baricos et al. (1988), "Degradation of glomerular basement membrane by purified mammalian metalloproteinases," Biochem. J. 254:609–612.

Bernstein et al. (1985), "Preparation of a diketopiperazine analog of leukotriene $D_4$ ($LT_4$)," Tet. Lett. 26(14):1951–1954.

Beyermann et al. (1990), "Rapid continuous peptide synthesis via FMOC amino acid chloride coupling and 4–(aminomethyl)piperidine deblocking," J. Org. Chem. 55:721–728.

Birkedal–Hansen et al. (1993), "Matrix metalloproteinases: A review," Critical Reviews in Oral Biology and Medicine 4(2):197–250.

Blanckaert et al. (1989), "Direct extraction and assay of collagenase from human osteoarthritic articular cartilage," Clinica Chimica Acta 185:73–80.

Borenfreund et al. (1974), "Chromosomal aberrations induced by hypo–nitrite and hydroxylamine derivatives," J. Natl. Cancer Inst. 32:667–679.

Brenner et al. (1989), "Genes for extracellular matrix–degrading metalloproteinases and their inhibitor, TIMP, are expressed during early mammalian development," Genes & Develop. 3:848–859.

Brown et al. (1969), "Collagenolytic activity of alkali–burned corneas," Arch. Ophthal. 81:370–373.

Burns et al. (1989), "Inhibition of purified collagenase from alkali–burned rabbit corneas," Invest. Opthalmol. 30:1569–1575.

Caputo et al. (1988), "Protease inhibitors decrease rabbit cartilage degradation after meniscectomy," J. Orthop. Res. 6:103–108.

Case et al. (1989), "Transin/stromelysin expression in the synovium of rats with experimental erosive arthritis," J. Clin. Invest. 84:1731–1740.

Delaisse et al. (1985), "A new synthetic inhibitor of mammalian tissue collagenase inhibits bone resorption in culture," Biochem. Biophys. Res. Commun. 133:483–490.

Dudman et al. (1982), "Homocysteine thiolactone and experimental homocysteinemia," Biochem. Med. 27:244–253.

(List continued on next page.)

Primary Examiner—Bruck Kifle
(74) Attorney, Agent, or Firm—Elaine C. Stracker; William B. Kezer

(57) ABSTRACT

Novel inhibitors of metalloproteases, in particular collagenase-1 and stromelysin-1, are disclosed. Such compounds are useful in pharmaceutical compositions and methods for treating or controlling disease states or conditions which involve tissue breakdown, such as rheumatoid arthritis.

14 Claims, No Drawings

OTHER PUBLICATIONS

Fishbein et al. (1963), "Hydroxyurea: Mechanism of action," Science 142:1069–1070.

Gillissen et al. (1992), "Sulfation of hydroxylamines and hydroxamic acids in liver cytosol from male and female rats and purified aryl sulfotransferase IV," Carcinogenesis 13:1699–1703.

Gillissen et al. (1994), "Sulfation of aromatic hydroxamic acids and hydroxylamines by multiple forms of human liver sulfotransferases," Carcinogenesis 15:39–45.

Hasty et al. (1990), "The role of stromelysin in the cartilage destruction that accompanies inflammatory arthritis," Arthr. Rheum. 33:388–397.

Henney et al. (1991), "Localization of stromelysin gene expression in atherosclerotic plaques by in situ hybridization," Proc. Natl. Acad. Sci. USA 88:8154–8158.

Ito et al. (1988), "Evidence that human rheumatoid synovial matrix metalloproteinase 3 is an endogenous activator of procollagenase," Arch. Biochem. Biophys. 267:211–216.

Johnson et al. (1987), "Collagenase inhibitors: Their design and potential therapeutic use," J. Enzym. Inhib. (1987), 2:1–22.

Krane et al. (1988), "Modulation of matrix synthesis and degradation in joint inflammation," in The Control of Tissue Damage, A.B. Glauert (ed.), Elsevier Sci. Publ., Amsterdam, Ch. 14, pp. 179–195.

Kronberger et al. (1982), "Enhanced cell–free translation of human skin collagenase in recessive dystrophic epidermolysis Bullosa," J. Invest. Dermatol. 79:208–211.

Liotta et al. (1983), "Tumor invasion and the extracellular matrix," Lab. Invest. 49:636–649.

Matrisian et al. (1986), "The mRNA coding for the secreted protease transin is expressed more abundantly in malignant than in benign tumors," Proc. Natl. Acad. Sci. USA 83:9413–9417.

Murphy et al. (1987), "Stromelysin is an activator of procollagenase," Biochem. J. 248:265–268.

Musser et al. (1986), "Synthesis of (Naphthalenylmethoxy)–and (Quinolinylmethoxy)phenyl amino oxoalkanoic acid esters,"J. Med. Chem. 29:1429–1435.

Nachev (1992), "Synthesis of N–polyfunctional substituted L–phenylalanine and S–methyl–L–cysteine containing the organophosphoric acid residue and their enzyme–substrate interaction," Chem. Abstracts, vol. 117, No. 33, Abstract No. 70275b, pp. 849.

Natchev (1991), "Synthesis of N–polyfunctional substituted L–phenylalanine and S–methyl–L–cysteine containing the organophosphoric acid residue and their enzyme–substrate interaction," Bulgarian Academy of Sciences, Communications of the Department of Chemistry vol. 24, No. 1, pp. 3–17.

Ogata et al. (1992), "Matrix metalloproteinase 3 (stromelysin) activates the precursor for the human matrix metalloproteinase 9," J. Biol. Chem. 267:3581–3584.

Okada et al. (1990), "Matrix metalloproteinase 2 from human rheumatoid synovial fibroblasts," Eur. J. Biochem. 194:721–730.

Overall et al. (1987), "Demonstration of tissue collangenase activity in vivo and its relationship to inflammation severity in human gingiva," J. Periodontal Res. 22:81–88.

Reich et al. (1988), "Inhibitors of collagenase IV and cell adhesion reduce the invasive activity of malignant tumour cells," in Metastasis: Ciba Foundation Symposium, Wiley, Chichester, pp. 193–210.

Richter et al. (1996), "Penicillamide: An extractable chiral auxiliary providing excellent stereocontrol," Tetrahedron: Asymmetry 7(2):427–434.

Rodman et al. (1987), "Hypercoagulability produced by treatment with acetohydroxamic acid," Clin. Pharmacol. Ther. 42:346–350.

Rossbach et al. (1971), "Synthesis and properties of unsymmetrical diketopiperazines of cysteine," Abstract, Physiol. Chem. Inst., University Tuebingen, Tuebingen, Germany, Z. Naturforsch B, 26(11):1144–1151.

Sawamura et al. (1991), "Increased gene expression of matrix metalloproteinase–3 (stromelysin) in skin fibroblasts from patients with severe recessive dystrophic epidermolysis bullosa," Biochem. Biophys. Res. Commun. 174:1003–1008.

Schneider et al. (1969), "Kinetics of the reaction of imidazole–SH compounds with N–ethylmaleimide," Hoppe–Seyler's Z. Physiol. Chem. Bd. 350, S. 1521–1530.

Shaw et al. (1988), "Small substrates and inhibitors of the metalloproteoglycanase of rabbit articular chondrocytes," Adv. Inflam. Res. 12:67–79.

Too et al. (1984), "Relaxin increases the release of plasminogen activator, collagenase, and proteoglycanase from rat granulosa cells in vitro," Endocrin. 115:1043–1050.

Uitto et al. (1981), "Collagenase and neutral metallo–proteinase activity in extracts of inflamed human gingiva," J. Periodontal Res. 16:417–424.

Vincenti et al. (1994), "Using inhibitors of metalloproteinases to treat arthritis," Arthritis & Rheumatism 37:1115–1126.

Vine et al. (1991), "Metalloproteinases in degenerative aortic disease," Clin. Sci. 81:233–239.

Whitham et al. (1986), "Comparison of human stromelysin and collagenase by cloning and sequence analysis," Biochem. J. 240:913–916.

Wilhelm et al. (1987), "Human skin fibroblast stromelysin: Structure, glycosylation, substrate specificity, and differential expression in normal and tumorigenic cells," Proc. Natl. Acad. Sci. USA 84:6725–6729.

Williams et al. (1984), "A randomized double–blind study of acetohydroxamic acid in struvite nephrolithiasis," N. Engl. J. Med. 311:760–764.

Williams et al. (1990), "Septic arthritis," Arthr. Rheum. 33:533–541.

Winyard et al. (1991), "Proteolytic inactivation of human $\alpha 1$ antitrypsin by human stromelysin," FEBS Letts. 279(1):91–94.

Woessner et al. (1989), "Connective tissue Breakdown in ovulation," Steroids 54:491–499.

Yoshioka et al. (1986), "Mutagenicity of N–arylacetohydroxamic acids and their O–glucosides derived from chlorinated 4–nitrobiphenyl ethers," Mutat. Res. 170:93–102.

COLLAGENASE-1 AND STROMELYSIN-1 INHIBITORS, PHARMACEUTICAL COMPOSITIONS COMPRISING SAME AND METHODS OF THEIR USE

CROSS-REFERENCE

This application is a continuation of U.S. application Ser. No. 08/665,603, filed Jun. 18, 1996 (now U.S. Pat. No. 5,932,579).

BACKGROUND OF THE INVENTION

1. Field of the Invention

This invention relates to novel pharmaceutically active compounds which are inhibitors of metalloproteases. Pharmaceutical compositions comprising these compounds as well as methods of their use for treating or controlling disease states or conditions associated with such enzymes are also described.

2. State of the Art

Metalloproteases are involved in a large number of disease states and other conditions in human and other animals. The metalloproteases are a family of enzymes containing zinc at the active site, which facilitates the catalytic hydrolysis of various protein substrates. A subfamily of the metalloprotease family is known as the matrix metalloproteases because these enzymes are capable of degrading the major components of articular cartilage and basement membranes. The matrix metalloproteases include stromelysin, collagenase, matrilysin and gelatinase, among others.

Stromelysin (aka. proteoglycanase, matrix metalloproteinase-3, MMP-3, procollagenase activator, "transin"), collagenase (aka. interstitial collagenase, matrix metalloproteinase-1, MMP-1, type II collagenase), and gelatinase (aka. type IV collagenase, matrix metalloproteinase-2, MMP-2, 72 kDa-gelatinase or type V collagenase, matrix metalloproteinase-9, MMP-9, 95 kda-gelatinase) are metalloendoproteinases secreted by fibroblasts and chondrocytes, and are capable of degrading the major connective tissue components of articular cartilage or basement membranes. Human rheumatoid synovial collagenase is approximately 50% identical to human stromelysin (Whitham et al., *Biochem. J.*, 240:913–916 (1986)). Gelatinase (MR ~72,000) has been isolated from rheumatoid fibroblasts (Okada et al., *Eur. J. Biochem.*, 194:721–730 (1990)). A higher molecular weight gelatinase (MR ~95,000; aka. type-V collagenase, matrix metalloproteinase-9, MMP-9) is also secreted by fibroblasts and monocytes and may be involved in cartilage degradation.

Metalloproteases are apparently involved in several arthritis conditions, including osteoarthritis (OA) and rheumatoid arthritis (RA). These diseases are largely due to the loss of articular cartilage. Elevated levels of stromelysin and collagenase have been detected in joints of arthritic humans and animals (Hasty et al., *Arthr. Rheum.*, 33:388–397 (1990); Krane et al., *In The Control of Tissue Damage*, A. B. Glauert (ed.), Elsevier *Sci. Publ., Amsterdam*, 1988, Ch. 14, pp. 179–195; Blanckaert et al., *Clin. Chim. Acta*, 185:73–80 (1989)). Each enzyme is secreted from these cells as an inactive proenzyme which is subsequently activated. There is evidence that stromelysin may be the in vivo activator for collagenase and gelatinase, implying a cascade for degradative enzyme activity (Fo et al., *Arch. Biochem. Biophys.*, 267:211–216 (1988); Murphy et al., *Biochem. J.*, 248:265–268 (1987); Ogata et al., *J. Biol. Chem.*, 267:3581–3584 (1992)). The synthesis of the gelatinase proenzyme is not coordinately regulated with the other two metalloproteinases. The role of gelatinase in the tissue destruction of articular cartilage appears different from the other two enzymes.

Stromelysin and collagenase are also implicated in the articular cartilage damage associated with septic arthritis. Bacterial infections of the joints can elicit an inflammatory response that may then be perpetuated beyond what is needed for removal of the infective agent, resulting in permanent damage to structural components. Bacterial agents have been used in animal models to elicit an arthritic response with the appearance of proteolytic activities (Case et al., *J. Clin Invest.*, 84:1731–1740 (1989); Williams et al., *Arthr. Rheum.*, 33:533–541 (1990)).

Secreted proteinases such as stromelysin, collagenase, and gelatinase play an important role in processes involved in the movement of cells during metastatic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis.

Periodontal diseases such as gingivitis are also characterized by metalloprotease expression. Both collagenase and stromelysin activities have been isolated from fibroblasts isolated from inflamed gingiva (Uitto et al., *J. Periodontal Res.*, 16:417–424 (1981)). Enzyme levels have been correlated to the severity of gum disease (Overall et al., *J. Periodontal Res.*, 22:81–88 (1987)).

Stromelysin has been implicated in the degradation of structural components of the glomerular basement membrane (GBM) of the kidney, the major function of which is to restrict passage of plasma proteins into the urine (Baricos et al., *Biochem. J.*, 254:609–612 (1988)). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases.

Metalloproteases may also be involved in the rupturing of atherosclerotic plaques leading to coronary thrombosis. The tearing or rupturing of atherosclerotic plaques is the most common event initiating coronary thrombosis. Destabilization and degradation of the connection tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin messenger RNA have been found to be localized to individual cells in atherosclerotic plaques removed from heart transplant patients at the time of surgery (Henney et al., *Proc. Natl. Acad. Sci. USA*, 88:8154–8158 (1991)).

Degenerative aortic disease associated with thinning of the medial aortic wall is another condition in which matrix metalloproteases may play a role. Aneurysms are often associated with atherosclerosis in this tissue. Increased levels of the matrix metalloproteinases have been identified in patients with aortic aneurysms and aortic stenosis (Vine et al., *Clin. Sci.*, 81:233–239 (1991)).

Expression of metalloproteinases, including stromelysin and collagenase, is observed in unfertilized eggs and zygotes and at further cleavage stages and increased at the blastocyst stage of fetal development and with endoderm differentiation (Brenner et al., *Genes & Develop.*, 3:848–859 (1989)). By analogy to tumor invasion, a blastocyst may express metalloproteinases in order to penetrate the extracellular matrix of the uterine wall during implantation. In addition, evidence exists that collagenase is important in ovulation processes. Collagenase apparently facilitates penetration of a covering of collagen over the apical region of the follicle, allowing the ovum to escape. There may also be a role for stromelysin activity during ovulation (Too et al., *Endocrin.* 115:1043–1050 (1984)).

Proteolytic processes have also been observed in the ulceration of the cornea following alkali burns (Brown et al., *Arch. Ophthalmol.*, 81:370–373 (1969)). Collagenolytic and stromelysin activity have also been observed in dystrophobic epidermolysis bullosa (Kronberger et al., *J. Invest. Dermatol.*, 79:208–211 (1982); Sawamura et al., *Biochem. Biophys. Res. Commun.*, 174:1003–1008 (1991)).

In addition to degrading structural components of the extracellular matrix, stromelysin can degrade other in vivo substrates, including the $\alpha_1$-proteinase inhibitor, and may therefore influence the activities of other proteinases such as elastase (Winyard et al., *FEBS Lett.*, 279(1):91–94 (1991)).

Because metalloproteases play a role in so many diseases and other conditions, inhibitors of these enzymes have been studied as possible therapeutic agents. In vitro experiments measuring the effect of matrix metalloendoproteinase inhibitors on proteoglycan release from rabbit cartilage explants suggest that stromelysin inhibition may be effective in preventing articular cartilage degradation (Caputo et al., *J. Orthopedic Res.*, 6:103–108 (1988)). Evidence also suggests that inhibitors of stromelysin, collagenase, and gelatinase will be useful to control tumor metastasis (Matrisian et al., *Proc. Natl. Acad. Sci. USA*, 83:9413–9417 (1986); Wilhelm et al., *Proc. Natl. Acad. Sci. USA*, 84:6725–6729 (1987); Liotta, et al., *Lab. Invest.*, 49:636–649 (1983); Reich et al., "Inhibitors of collagenase IV and cell adhesion reduce the invasive activity of malignant tumor cells", in *Metastasis: Ciba Foundation Symposium*; Wiley, Chichester, 1988, pp. 193–210). An inhibitor of collagenase has been shown to be effective in preventing ovulation (Woessner et al., *Steroids*, 54:491–499 (1989)). Mercapto-containing peptides inhibit the collagenase isolated from alkali-burned rabbit cornea (Burns et al., *Invest. Ophthalmol.*, 30:1569–1575 (1989)).

Thiol carboxylic acid derivatives that inhibit collagenase are disclosed in U.S. Pat. Nos. 5,109,000; 4,595,700; 4,371, 466. Additional collagenase inhibitor compounds are disclosed in European Patent Application Publication Nos. 0 423 943; 0 273 689; 0 322 184; and 0 185 380, and in International Patent Application Publication Nos. WO 88/06890 and WO 94/07481.

Collagenase inhibitors have also been designed around the cleavage site of the a-chain sequence of Type II collagen (Johnson et al., *J. Enzym. Inhib.*, 2:1–22 (1987)). One such inhibitor, N-[3-(benzyloxy-carbonyl)amino-1-carboxy-n-propyl]-L-leucyl-O-methyl-L-tyrosine, N-methylamide, prepared at G.D. Searle, Inc., is a potent inhibitor of human rheumatoid synovial collagenase (IC$_{50}$=0–8 $\mu$M). This compound also inhibits rabbit bone proteoglycanase (IC$_{50}$=0.5 $\mu$M) (Delaisse et al., *Biochem. Biophys. Res. Commun.*, 133:483–90 (1985)).

However, significant obstacles continue to stand in the way of clinical exploitation of metalloprotease inhibitors. First, there is very little to guide one in developing a specific inhibitor for each enzyme. In preliminary studies of rabbit proteoglycanase with substrates and inhibitors, little was found to indicate the enzyme's requirements for hydrolysis or inhibition beyond a preference for hydrophobic residues at the P$_1$' position (Shaw et al., *Adv. Inflam. Res.*, 12:. 67–79 (1988)). More extensive studies with a series of substrates revealed that stromelysin will tolerate nearly every amino acid residue around the scissile bond (Fields et al., unpublished results presented at the Matrix Metalloproteinase Conference, September 1989, Sandestin, Fla.).

Toxicity is a second obstacle to therapeutic use of previously known metalloprotease inhibitors. For example, certain hydroxamic acids have been suggested as collagenase inhibitors as in U.S. Pat. No. 4,599,361 and European Patent Application Publication No. 0 236 872. U.S. Pat. Nos. 5,304,604, 5,240,958 and 5,310,763 also disclose hydroxamic acid derivatives which act as inhibitors of metalloproteases involved in tissue degradation, such as collagenase, stromelysin (proteoglycanase), gelatinase and collagenase (IV).

Although these hydroxamic acid compounds are effective inhibitors of matrix metalloproteases, the hydroxamic acid moiety is potentially toxic. See, for example, Musser et al., *J. Med. Chem.*, 29:1429–1435 (1986); Baililien et al., *Am. J. Vet. Res.*, 74:2604–2611 (1986); Rodman et al., *R.L. Clin. Pharmacol. Ther.*, 42:346–350 (1987); Williams et al., *N. Engl. J. Med.*, 311:760–764 (1984); Yoshioka et al., *Mutat. Res.*, 170:93–102 (1986); Gillissen et al., *Carcinogenesis*, 15:39–45 (1994); Gillissen et al., *Carcinogenesis*, 13:1699–1703 (1992); Fishbein et al., *Science*, 142:1069–1070 (1963); and Borenfreund et al, *J. Nat. Cancer Inst*, 32:667–679 (1964). As a result, there are few, if any, hydroxamic acid based drugs in use.

The wide spectrum of clinical indications for matrix metalloprotease inhibitors establishes a clear need for matrix metalloprotease inhibitors that have satisfactory inhibition activity. It is not a simple matter, however, to predict what variations in known compounds would retain or even increase activity. The present invention fulfills this need for novel effective metalloprotease inhibitors.

SUMMARY OF THE INVENTION

The invention provides novel matrix metalloprotease inhibitors that are highly active. In one aspect, the present invention relates to a compound of formula:

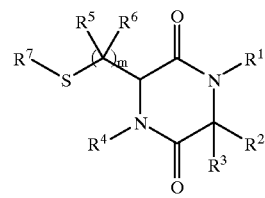

wherein $R^1$ and $R^4$ are independently selected from the group consisting of hydrogen and —CH$_2$R$^8$ and —CHR$^8$R$^9$;

$R^2$, $R^3$, $R^5$, $R^6$ and $R^8$ are independently selected from the group consisting of
(i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, $—SO_3$, $—SO_2NH_2$ and X is selected from the group consisting of a bond, O, and NR' where R' is as defined above;

(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, $—SO_3$, $—SO_2NH_2$ and Y is selected from the group consisting of a bond and NR' where R' is as defined above;

(v) alkenyl groups of from 2 to 10 carbon atoms;

(vi) alkynyl groups of from 3 to 10 carbon atoms;

(vii) carboxyl groups;

(viii) carboxyl ester groups wherein the ester group comprises from 1 to 12 carbon atoms;

(ix) heterocycles, either saturated, unsaturated, or aromatic, having from 2 to 6 carbon atoms and 1 to 3 ring hetero atoms selected from the group consisting of nitrogen, oxygen and sulfur, optionally substituted;

(x) R—C(O)— groups where R is hydrogen or an alkyl group of from 1 to 12 carbon atoms, optionally substituted on the alkyl group;

(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, $—SO_3$, $—SO_2NH_2$; and (xii) arylalkyl, optionally substituted on either the aryl group and/or the alkyl group; or wherein $R^2$, $R^3$ and the carbon to which they are attached form a cycloalkyl or heterocyclic group; or $R^1$ and $R^2$ and the carbon and nitrogen to which they are attached, respectively, form a heterocyclic group; or $R^4$ and $R^5$ and the carbon and nitrogen to which they are attached, respectively form a heterocyclic group;

$R^7$ is selected from the group consisting of hydrogen and alkyl of from 1 to 12 carbon atoms, $R^8C(O)—$ and $R^8S—$ where $R^8$ is as defined above;

$R^9$ is hydrogen, alkyl, substituted alkyl, aryl, substituted aryl, heterocyclic or substituted heterocyclic; and n is an integer from 1 to 3.

Preferably, $R^4$, $R^5$ and $R^6$ are independently selected from the group consisting of hydrogen and lower alkyl.

Preferably, $R^1$ and $R^2$ are independently alkyl groups (including cycloalkyl), which may be optionally substituted.

In one preferred embodiment, $R^4$ is hydrogen and $R^1$ is $—CHR^8R^9$ where $R^8$ is an amido group such as —NR'C(O)R" and $—C(O)NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is $—C(O)NH_rR'_s$ where R' is alkyl, including cycloalkyl, substituted alkyl, aryl, substituted aryl, heterocyclic and substituted heterocyclic.

In another preferred embodiment, $R^1$ is hydrogen and $R^4$ is $—CHR^8R^9$ where $R^8$ is an amido group such as —NR'C(O)R" and $—C(O)NH_rR'_s$ where R' and R" are independently selected from hydrogen, alkyl, aryl, arylalkyl, or heteroaryl and where r=0–2, s=0–2 and r+s=2. In a particularly preferred embodiment, the amido group is $—C(O)NH_rR'_s$ where R' is alkyl, including cycloalkyl, substituted alkyl, aryl, substituted aryl, heterocyclic and substituted heterocyclic.

In still another preferred embodiment, $R^2$ includes alkaryl and substituted alkaryl groups including $—CH_2—C_6H_4Z$ where Z is hydroxy, alkyl, substituted alkyl, alkoxy, substituted alkoxy, amido, amino, aryloxy, carboxyl, halo, mercapto, cyano, nitro, $—SO_3$, $—SO_2NH_2$ at any location on the phenyl ($—C_6H_4$ ring).

Even more preferably, $R^1$ is cyclohexyl and $R_2$ is methylcyclohexyl.

Particularly preferred compounds include the compounds recited in Table I below including all isomers thereof (e.g., R and S stereo isomers, cis and trans positional isomers, etc.) In Table I, n is 1 and $R^3$, $R^4$, $R^5$, $R^6$ and $R^7$ are hydrogen.

TABLE I

| $R^1$ | $R^2$ | No. |
|---|---|---|
| cyclohexyl-$CH_2$— | cyclohexyl-$CH_2$— | 1 |
| (p-methoxy-φ)$CH_2$— | cyclohexyl-$CH_2$— | 2 |
| (2-quinolinyl)-$CH_2$— | cyclohexyl-$CH_2$— | 3 |
| (2-quinolinyl)-$CH_2$— | (p-nitro-φ)$CH_2$— | 4 |
| (p-methoxy-φ)$CH_2$— | (p-nitro-φ)$CH_2$— | 5 |
| $CH_3(CH_2)_2$— | (p-nitro-φ)$CH_2$— | 6 |
| cyclohexyl-$CH_2$— | $CH_3(CH_2)_2$— | 7 |
| (p-methoxy-φ)$CH_2$— | φ-$CH_2$— | 8 |
| (p-methoxy-φ)$CH_2$— | 3-($C_5H_4N$)$CH_2$— | 9 |
| (p-methoxy-φ)$CH_2$— | 4-($C_5H_4N$)$CH_2$— | 10 |
| (p-methoxy-φ)$CH_2$— | (m-nitro-φ)$CH_2$— | 11 |
| (p-methoxy-φ)$CH_2$— | (o-nitro-φ)$CH_2$— | 12 |
| (p-methoxy-φ)$CH_2$— | (p-cyano-φ)$CH_2$— | 13 |
| (p-methoxy-φ)$CH_2$— | (p-C(O)$NH_2$—φ)$CH_2$— | 14 |
| (p-methoxy-φ)$CH_2$— | (p-C(O)OH-φ)$CH_2$— | 15 |
| (p-methoxy-φ)$CH_2$— | (p-$NH_2$-φ)$CH_2$— | 16 |
| (p-methoxy-φ)$CH_2$— | (p-NHC(O)$CH_3$-φ)$CH_2$— | 17 |
| (p-methoxy-φ)$CH_2$— | (p-$SO_3$H-φ)$CH_2$— | 18 |
| (p-methoxy-φ)$CH_2$— | (p-$SO_2NH_2$-φ)$CH_2$— | 21 |
| (p-methoxy-φ)$CH_2$— | (p-$OCF_3$-φ)$CH_2$— | 20 |
| (p-methoxy-φ)$CH_2$— | -(p-$CF_3$-φ)$CH_2$— | 21 |
| —CH(CH$_2$CH$_3$)—C(O)NH-cyclohexyl | -(p-nitro-φ)$CH_2$— | 22 |
| —CH(CH$_2$CH$_3$)—C(O)NH-cyclohexyl | -(p-$CF_3$-φ)$CH_2$— | 23 |

In a second aspect, this invention relates to a pharmaceutical composition of matter comprising the compounds of the present invention in an amount effective to inhibit mammalian collagenase-1 and/or stromelysin-1 in mammals afflicted with a disease state in which collagenase-tissue is broken down by collagenase-1 and/or stromelysin-1 or is otherwise associated with collagenase-1 or stromelysin-1, which comprises administering to such an afflicted mammal a therapeutically effective amount of a collagenase-1 or stromelysin-1 inhibitor having the formula above. Such disease states involve, for example, arthritic diseases such as rheumatoid arthritis and osteoarthritis, septic arthritis, articular cartilage degradation, Reiter's syndrome, pseudogout, juvenile rheumatoid arthritis, scleroderma, soft tissue rheumatism, polychodritis and tendinitis for bone resorption diseases such as osteoporosis, Paget's disease, hyperparathyroidism and cholesteatoma; for the recessive classes of dystrophic epidermolysis bullosa where the disease is linked to the overproduction of collagenase-1 and/or stromelysin-1; for periodontal disease and related consequences of gingival collagenase production of PMNL collagenase-1 and/or stromelysin-1 production following cellular infiltration to inflamed gingiva; for ulceration including corneal, epidermal, or gastric ulceration and more specifically, for corneal ulceration induced by alkali or other burns, by radiation, by vitamin deficiency or retinoid deficiency; for degenerative aortic disease associated with thinning of the media aortic wall and thus the prevention of events leading to acute and often times fatal aortic aneurysms; for use as a birth control agent and for preventing ovulation; for glomerular disease (e.g., proteinuria), coronary thrombosis (e.g., atherosclerotic plagues), Crohn's disease, multiple sclerosis and the cachexia associated with cancer or human immunodeficiency virus infection; and optionally in combination with current chemotherapy and/or radiation, for systemic chemotherapy of cancer, as well as the promotion of wound healing.

A further aspect of the present invention is a method of inhibiting mammalian collagenase-1 and/or stromelysin-1 in mammals afflicted with a disease state in which collagen-tissue is broken down by collagenase-1 and/or stromelysin-1 or is otherwise associated with collagenase-1 or stromelysin-1, such as those therapeutic indications listed above.

DETAILED DESCRIPTION OF THE INVENTION

I. Terminology

"Collagenase-1" refers to mammalian instital collagenase-1 also known in the art as MMP-1. While other collagenases are known, they are not included in this definition of collagenase-1.

"Stromelysin-1 refers to the specific matrix metalloprotease identified in the art as stromelysin-1 which is sometimes referred to as MMP-3.

"Alkyl" refers to a cyclic, branched, or straight chain alkyl group containing only carbon and hydrogen, preferably having from 1 to 12 carbon atoms. This term is further exemplified by groups such as methyl, heptyl, $-(CH_2)_2-$, $-(CH_2)_q-$, $-(CH_2)_q-(C_6H_{11})$, wherein q is from 1 to 5, adamantyl, and the like.

"Substituted alkyl" refers to a cyclic, branched, or straight chain alkyl group of from 1 to 12 carbon atoms having from 1 to 3 substituents selected from the group consisting of halogen, alkoxy, substituted alkoxy, thioalkoxy, substituted thioalkoxy (optionally wherein the sulfur atom of the thioalkoxy or substituted thioalkoxy group is oxidized to the sulfinyl or sulfonyl derivative), acyl, acyloxy, amido, amino, N-alkylamino, N,N-dialkylamino, aminotosyl, t-butoxycarbonylamino, hydroxyl, mercapto, carboxy, carboxyalkyl, carboxamide, benzyloxy, heterocyclic, aryl, heteroaryl, and substituted aryl and substituted heterocyclic. The particular substituents for the substituent alkyl groups are selected to be "non-interfering" so as not to eliminate or severely decrease the metalloprotease inhibition activity of the compound.

"Alkoxy" refers to —O-alkyl and includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to —O-substituted alkyl and includes, by way of example, —OCF$_3$, —OCH$_2$—φ and the like.

"Amide" or "amido" refers to the groups —NR'C(O)R" and —C(O)NH$_r$R'$_s$ where R' and R" are independently selected from hydrogen, alkyl, aryl, arylalkyl, or heteroaryl and where r=0–2, s=0–2 and r+s=2 (including substituted alkyl, substituted aryl, substituted arylalkyl and substituted heteroaryl).

"Amino" refers to the group —NR'R", where R' and R" are independently hydrogen, alkyl, substituted alkyl, aryl or substituted aryl.

"Amino acid" refers to any of the naturally occurring amino acids, as well as synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). See, e.g., Harper et al (1977) *Review of Physiological Chemistry*, 16th Ed., Lange Medical Publications, pp. 21–24. One of skill in the art will appreciate that the term "amino acid" also includes β, γ-, δ-, and ω-amino acids, and the like. Unnatural amino acids are also known in the art, as set forth in, for example, Williams (ed.), Synthesis of Optically Active α-Amino Acids, Pergamon Press (1989); Evans et al., *J. Amer. Chem. Soc.*, 112:4011–4030 (1990); Pu et al., *J. Amer. Chem. Soc.*, 56:1280–1283 (1991); Williams et al., *J. Amer. Chem. Soc.*, 113:9276–9286 (1991); and all references cited therein.

As used herein, the twenty conventional amino acids and their abbreviations follow conventional usage (see IMMUNOLOGY-A SYNTHESIS, 2nd Edition, E. S. Golub and D. R. Gren, Eds., Sinauer Associates, Sunderland, Mass. (1991), which is incorporated herein by reference). Amino acid residues are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Stereoisomers (e.g., D-amino acids) of the twenty conventional amino acids, unnatural amino acids such as α,α-disubstituted amino acids, N-alkyl amino acids, and other unconventional amino acids may also be suitable components for compounds of the present invention. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

"Aryl" or "Ar" refers to an unsaturated aromatic carbocyclic group of from 6 to 14 carbon atoms having a single ring (e.g., phenyl) or multiple condensed rings (e.g., naphthyl or anthryl) carbon atoms, which can optionally be unsubstituted or substituted with from 1 to 3 substituents selected from hydroxy, alkyl, substituted alkyl, alkoxy, substituted alkoxy, amido, amino, aryloxy, carboxyl, halo, mercapto, cyano, nitro, —SO$_3$, —SO$_2$NH$_2$ and other non-interfering substituents. Preferred aryls include phenyl and alkyl substituted phenyl.

"Arylalkyl" refers to the groups —R—Ar and —R—HetAr, where Ar is an aryl group (including substituted aryl groups), HetAr is a heteroaryl group (including substituted heteroaryl groups) and R is a straight-chain or branched-chain alkyl group or substituted alkyl group. Examples of arylalkyl groups include benzyl, —CH$_2$CH$_2$φ, and furfuryl. Benzyl is preferred.

"Carboxy" or "carboxylic acid" refers to the group —COOH.

"Ester" or "carboxyl ester" refers to the group —C(O)OR where R is alkyl, aryl, arylalkyl, or heteroaryl (including substituted alkyl, substituted aryl, substituted heteroaryl, or substituted arylalkyl).

"Halo" or "halogen" refers to fluoro, chloro, bromo and iodo and preferably is either chloro or bromo.

"Heterocycle" or "heterocyclic" refers to a monovalent saturated, unsaturated or aromatic (heteroaryl) carbocyclic group having a single ring or multiple condensed rings having at least one hetero atom, such as nitrogen, sulfur or oxygen within the ring, which can optionally be unsubstituted or substituted with from 1 to 3 substituents selected from the group consisting of hydroxy, alkyl, substituted alkyl, alkoxy, substituted alkoxy, aryl, substituted aryl, halo, mercapto, and other non-interfering substituents. Preferably, heterocycles are from 1 to 12 carbon atoms and from 1 to 4 hetero atoms.

"Heteroaryl" or "HetAr" refers to a monovalent aromatic heterocyclic group having a single ring (e.g., pyridyl or furyl) or multiple condensed rings (e.g., indolizinyl or benzo[b]thienyl). Preferably, the heteroaryl has from 2 to 12 carbon atoms and 1 to 4 heteroatoms selected from oxygen, nitrogen and sulfur within the ring which can optionally be substituted with from 1 to 3 substituents selected from the group consisting of hydroxy, alkyl, substituted alkyl, alkoxy, substituted alkoxy, aryl, substituted aryl, halo, mercapto, and other non-interfering substituents.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, and indoline. Preferred heteroaryls include pyrrole and pyridine.

"Hydroxy" or "hydroxyl" refers to the group —OH.

"Mercapto", "sulphydryl", or "thiol" refers to the group —SH.

"Protecting group" refers to a chemical group which generally exhibits the following characteristics: 1) the group must react selectively with the desired functionality in good yield to give a derivative that is stable to future projected reactions; 2) the protecting group must be selectively removable from the protected substrate to yield the desired functionality; and 3) the protecting group must be removable in good yield by reagents that do not attack one or more of the other functional group(s) generated or present in the projected reaction(s). Examples of protecting groups can be found in Greene et al. (1991) *Protective Groups in Organic Synthesis*, 2nd Ed. (John Wiley & Sons, Inc., New York).

Sidechain protecting groups may be used for certain amino acid derivatives having reactive functionalities, such as hydroxyl, carboxyl, amino, mercapto, guanidino, imidazolyl, indolyl and the like. The particular protecting groups used for any functional group requiring protection are generally known in the art. Exemplary sidechain protecting groups are acetyl, benzoyl, benzyl, t-butyl, and the like for hydroxyl; cyclohexyl, benzyl, methyl, ethyl, t-butyl, and the like for carboxyl; benzyl, 4-methylbenzyl, 4-methoxybenzyl, acetyl, acetamidomethyl, trephenylmethyl (trityl) and the like for mercapto; t-butyoxycarbonyl (Boc), benzyloxycarbonyl (Cbz), 9-fluroenylmethoxycarbonyl (Fmoc), phthaloyl (Pht), P-toluenesulfonyl (Tos), trifluoroacetyl, 2-(trimethylsilyl)-ethoxycarbonyl (TEOC), and the like for amino; 2,4-dinitrophenyl, benzyloxymethyl, Tos, Boc, Trityl, and the like for imidazolyl; formyl, Cbz, TEOC, 2,2,2-trichloroethyl carvamate (TROC), and the like for indolyl; and tosyl, nitro, bis(1-adamantyloxycarbonyl) and the like for guanidino.

Functional group protecting groups may be removed, if desired, by treatment with one or more deprotecting agents in an inert solvent of solvent mixture. For examples of protecting groups and suitable deprotecting agents, see Bodansky, M. and Bodansky, A., *The Practice of Peptide Synthesis*, Springer-Verlag, Inc. (1984); and Greene, T. W. and Wuts, P., *Protective Groups in Organic Synthesis* (2d ed.), John Wiley & Sons, Inc. (1991).

"Substituted" as applied to any moiety preferably means substituted with one or more (typically up to five) substituents selected from the group consisting of:

alkoxy of from 1 to 12 carbon atoms in an alkyl group, alkenyl groups of from 2 to 10 carbon atoms, alkynyl groups of from 3 to 10 carbon atoms, hydroxyl, halo, cycloalkyl of from 3 to 8 carbon atoms, cyano, nitro, amino, mono- and di-alkylamines of from 1 to 12 carbon atoms in each alkyl group,

—SH,

—SR where R is an alkyl group of from 1 to 12 carbon atoms, carboxyl, carboxyl esters of from 1 to 12 carbon atoms in the ester moiety, —NR'C(O)—X—R" where R' and R" are independently selected from the group consisting of hydrogen and alkyl of from 1 to 12 carbon atoms, aryl or heteroaryl groups optionally substituted with from 1 to 3 substituents on the aryl or heteroaryl moiety selected from the group consisting of halo, hydroxyl, amino, cyano, carboxyl, nitro, alkyl of from 1 to 12 carbon atoms, and alkoxy of from 1 to 12 carbon atoms (preferred aryl groups have from 6 to 10 carbon atoms and preferred heteroaryl groups have from 2 to 9 carbon atoms and from 1 to 3 ring hetero atoms selected from the group consisting of nitrogen, oxygen and sulfur and X is selected from the group consisting of a bond, O and NR' where R' is as defined above.

II. The Compounds

The present invention provides compounds of the following formula:

Formula I

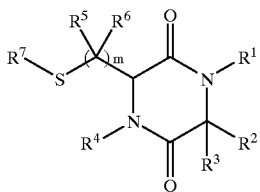

wherein $R^1$ and $R^4$ are independently selected from the group consisting of hydrogen and —$CH_2R^8$ and —$CHR^8R^9$;

$R^2, R^3, R^5, R^6$ and $R^8$ are independently selected from the group consisting of
(i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and X is selected from the group consisting of a bond, O, and NR' where R' is as defined above;
(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$ and Y is selected from the group consisting of a bond and NR' where R' is as defined above;
(v) alkenyl groups of from 2 to 10 carbon atoms;
(vi) alkynyl groups of from 3 to 10 carbon atoms;
(vii) carboxyl groups;
(viii) carboxyl ester groups wherein the ester group comprises from 1 to 12 carbon atoms;
(ix) heterocycles, either saturated, unsaturated, or aromatic, having from 2 to 6 carbon atoms and 1 to 3 ring hetero atoms selected from the group consisting of nitrogen, oxygen and sulfur, optionally substituted;
(x) R—C(O)— groups where R is hydrogen or an alkyl group of from 1 to 12 carbon atoms, optionally substituted on the alkyl group;
(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, —$SO_2NH_2$; and
(xii) arylalkyl, optionally substituted on either the aryl group and/or the alkyl group; or wherein $R^2, R^3$ and the carbon to which they are attached form a cycloalkyl or heterocyclic group; or $R^1$ and $R^2$ and the carbon and nitrogen to which they are attached, respectively, form a heterocyclic group; or $R^4$ and $R^5$ and the carbon and nitrogen to which they are attached, respectively form a heterocyclic group;

$R^7$ is selected from the group consisting of hydrogen and alkyl of from 1 to 12 carbon atoms, $R^8C(O)$— and $R^8S$— where $R^8$ is as defined above;

$R^9$ is hydrogen, alkyl, substituted alkyl, aryl, substituted aryl, heterocyclic or substituted heterocyclic; and n is an integer from 1 to 3.

Preferably, $R^4, R^5$ and $R^6$ are independently selected from the group consisting of hydrogen and lower alkyl.

Preferably, $R^1$ and $R^2$ are independently alkyl groups (including cycloalkyl), which may be optionally substituted.

In one preferred embodiment, $R^4$ is hydrogen and $R^1$ is —$CHR^8R^9$ where $R^8$ is an amido group such as —NR'C(O)R" and —C(O)NH$_r$R'$_s$ where R' and R" are independently selected from hydrogen, alkyl, aryl, arylalkyl, or heteroaryl and where r=0–2, s=0–2 and r+s=2. In a particularly preferred embodiment, the amido group is —C(O)NH$_r$R'$_s$ where R' is alkyl, including cycloalkyl, substituted alkyl, aryl, substituted aryl, heterocyclic and substituted heterocyclic.

In another preferred embodiment, $R^1$ is hydrogen and $R^4$ is —$CHR^8R^9$ where $R^8$ is an amido group such as —NR'C(O)R" and —C(O)NH$_r$R'$_s$ where R' and R" are independently selected from hydrogen, alkyl, aryl, arylalkyl, or heteroaryl and where r=0–2, s=0–2 and r+s=2. In a particularly preferred embodiment, the amido group is —C(O)NH$_r$R'$_s$ where R' is alkyl, including cycloalkyl, substituted alkyl, aryl, substituted aryl, heterocyclic and substituted heterocyclic.

In still another preferred embodiment, $R^2$ includes alkaryl and substituted alkaryl groups including —$CH_2$—$C_6H_4Z$ where Z is hydroxy, alkyl, substituted alkyl, alkoxy, substituted alkoxy, amido, amino, aryloxy, carboxyl, halo, mercapto, cyano, nitro, —$SO_3$, —$SO_2NH_2$ at any location on the phenyl (—$C_6H_4$ ring).

Even more preferably, $R^1$ is cyclohexyl and $R_2$ is methylcyclohexyl. Particularly preferred compounds include the compounds recited in Table I above.

As used herein, compounds of the present invention include derivatives of the above compound of Formula I, having any substitutions which do not eliminate or significantly reduce their ability to bind metalloproteases. For example, as previously stated, the compounds of the present invention are optionally substituted with a functional group. Any art-recognized functional group which does not eliminate or significantly reduce the compound's ability to bind metalloproteases are contemplated, including, but not limited to ester, amide acid, amine, alcohol, ether, and thioether, etc. Symmetrical and asymmetrical disulfides are also specifically included in the compounds of the present invention.

In addition, compounds of this invention can, depending on the nature of the functional groups, form addition salts with various inorganic and organic acids and bases. Pharmaceutical salts of the compounds of the present invention suitable for administration by a variety of routes are known in the art and need not be described herein in detail. Pharmaceutically acceptable salts include, but are not limited to, salts of (1) organic carboxylic acids such as acetic acid, propionic acid, glycolic acid, pyruvic acid, oxalic acid, malic acid, malonic acid, succinic acid, maleic acid, fumaric acid, tartaric acid, citric acid, cinnamic acid, mandelic acid, salicylic acid, benzoic acid, lactic, tartaric, isothionic, lactobionic and succinic acids; organic sulfonic acids such as methanesulfonic, ethanesulfonic, benzenesulfonic and p-toluylsulfonic acids; (2) inorganic acids such as hydrogen halide acids (e.t., hydrochloric acid and hydrobromic acid), sulfuric acid, nitric acid, and phosphoric acid; (3) alkali metals such as lithium, sodium and potassium. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium), ammonium, and $NW_xH_y$ bases and salts wherein each of x and y are 0 to 4 and x+y is 4, and wherein W is a ($C_1$–$C_{18}$) alkyl. Salts can also be formed from a carboxylic acid and an organic base, such as trimethylamine, diethylamine, ethanolamine, piperidine, isopropylamine, choline, caffeine, and the like.

Solvates, e.g., hydrates, of the compounds of the present invention are also included within the scope of the present invention. Methods of solvation to produce such solvates are generally known in the art.

The present invention also includes prodrugs of the compounds of Formula I. Various forms of prodrugs are well known in the art, for example, as discussed in Bundgaard (ed.), *Design of Prodrugs*, Elsevier (1985); Widder et al. (ed.), *Methods in Enzymology*, vol. 42, Academic Press, 309–396 (1985); Krogsgaard-Larsen et al. (ed.), "Design and Application of Prodrugs", *Textbook of Drug Design and Development*, Chapter 5, 113–191 (1991); Bundgaard, *Advanced Drug Delivery Reviews*, 8:1–38 (1992); Bundgaard et al., *Journal of Pharmaceutical Sciences*, 77:285 (1988); and Kakeya et al., *Chem. Pharm. Bull.*, 32:692 (1984).

There are several chiral centers in the compounds of the present invention because of the presence of asymmetric carbon atoms. The presence of several asymmetric carbon atoms gives rise to a number of diastereomers with the appropriate R or S stereochemistry at each chiral center. Compounds of Formula I and, where appropriate, all other formulae in this specification, including the claims, are to be understood to include all such individual stereoisomers and mixtures (for example, racemic mixtures) thereof.

II. Preparation

Compounds of the present invention can be readily prepared by either solution phase or solid phase synthetic techniques. For example, a preferred solution phase synthesis is outlined in the following reaction scheme:

Reaction Scheme I

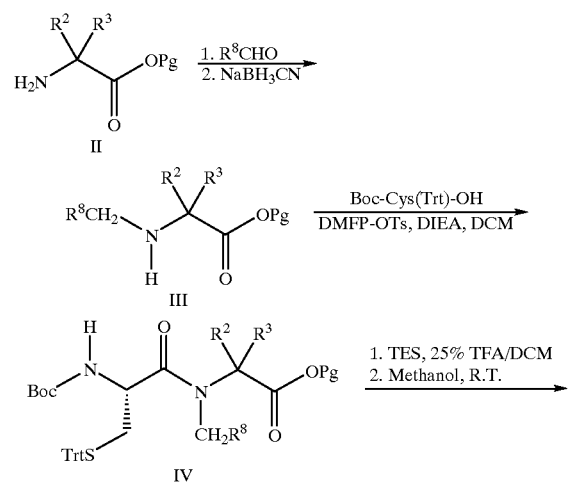

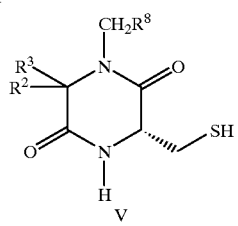

In one embodiment, reductive alkylation of an alpha amino acid of Formula II bearing an appropriate carboxyl protecting group yields a compound of Formula III, wherein $R^2$, $R^3$, and $R^8$ are as defined above. The reaction is preferably carried out in the presence of trimethylorthoformate and sodium cyanoborohydride. The amino acid Boc-Cys(Trt)-OH can optionally contain a single suitable substituent ($R^4$) on the amino group, e.g., an alkyl group, such that the resulting product V will contain a $R^4$ substituent replacing the hydrogen of the NH group.

The corresponding dipeptide can be produced by treatment of the N-alkylated amino acid of Formula III with an appropriately protected cysteine derivative. The reaction is preferably carried out in the presence of a coupling agent, for example DMFP.

Deprotection and cyclization affords the desired diketopiperazine V which is a compound of Formula I.

In another embodiment, the dipeptide is prepared by conducting reductive amination via coupling the aldehyde (i.e., $R^8CHO$) with an appropriately protected cysteine derivative followed by reaction of the amine with a protected suitable amino acid (i.e., $PgNCR^2R^3COOH$). Deprotection and cyclization affords the desired diketopiperazine of formula

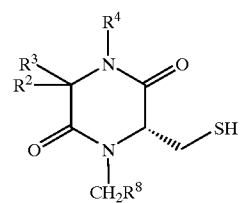

In either case, after deprotection, the terminal amino group can be alkylated prior to cyclization to provide for alkylated derivatives. Such alkylated groups include those recited above for the —$CH_2R^8$ derivatives.

The compounds of Formula II are either known amino acid derivatives or can be made from these derivatives by known methods. For example, the acid addition salt of compounds of Formula II can be treated with weak aqueous base (e.g., 5% aqueous sodium carbonate) to yield the corresponding free amine.

The intermediates of Formulas III and IV disclosed herein are in some forms novel compounds and form an aspect of the present invention as do the described processes for their preparation.

As mentioned above, the compounds of Formula I may exist in more than one diastereomeric form. Where the processes of the invention produce mixtures thereof, the individual isomers may be separated one from another by chromatography, e.g., HPLC.

Alternatively, separate diastereomeric compounds of Formula I can be obtained by using stereoisomerically pure starting materials or by separating desired isomers of intermediates at any stage in the overall synthetic process and converting these intermediates to compounds of Formula I.

The preparation of compounds of Formula I, wherein $R^1$ is —$CH_2R^8$ and $R^8$ is cyclohexy, $R^2$ is methylcyclohexyl, and $R^3$, $R^4$, $R^5$, and $R^6$ are hydrogen, from compounds of Formula V is further illustrated in Reaction Scheme 2.

Reaction Scheme 2

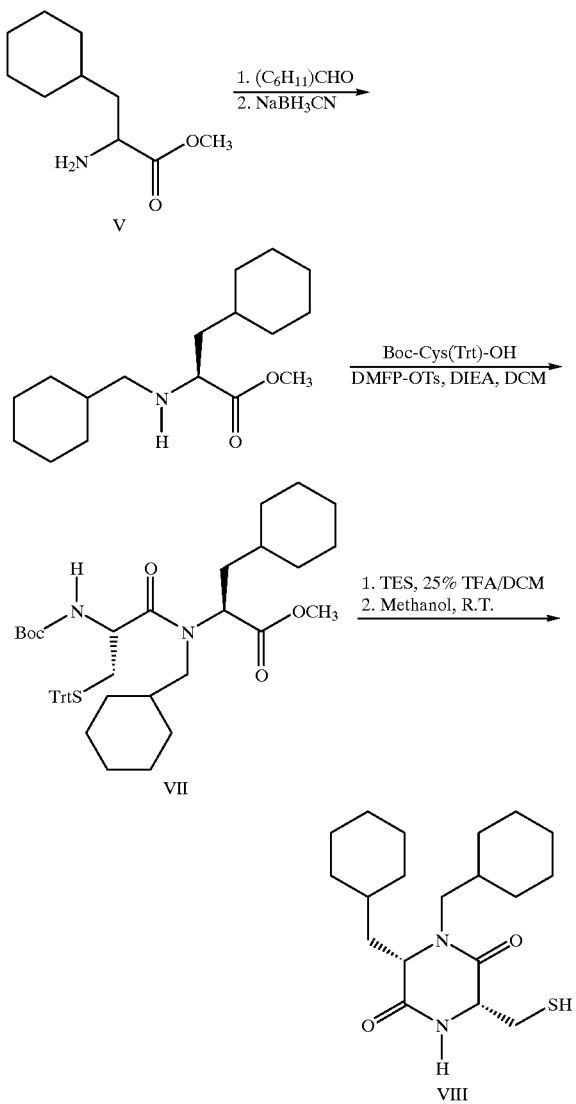

A single N-alkylated diketopiperazine of the present invention or a library of diketopiperazine derivatives also can be prepared under solid phase conditions, as described in copending applications: PCT patent application PCT/US95/07964; U.S. Ser. No. 08/265,578, filed Jun. 23, 1994; U.S. Ser. No. 08/393,318, filed Feb. 22, 1994; and U.S. Ser. No. 08/518,839, each of which is incorporated herein by reference for all purposes.

In the reaction schemes set forth above, the $R^1$ or $R^4$ substituent is necessarily —$CH_2R^8$ because the reaction proceeds from an imine which upon reduction, yields a methylene group adjacent to the nitrogen atom.

In another synthetic embodiment, diketopiperazines can be prepared via the known Ugi procedure, Ugi, et al. Comprehensive Organic Synthesis for Synthetic Efficiency, 20:1083 (1991). In this procedure, four components are combined, namely an amine (e.g., a first amino acid which can optionally be covalently linked to a solid support through the carboxyl group or having the carboxyl group protected), a carbonyl component (e.g., an aldehyde or ketone), an acid (e.g., a second amino acid having the amine group blocked or optionally can be covalently linked to a solid support) and an isocyanide.

Without being limited to any theory, it is believed that the reaction mechanism proceeds via formation of an imine from the amine component and the carbonyl component. The imine is then protonated by the acid to give the iminium ion. Nucleophilic attack of the isocyanide is followed by addition of the carboxylate component yielding an α-adduct that spontaneously rearranges into a stable α-acylaminocarboxamide. This rearrangement takes place only if a primary amine is employed. Secondary amines yield diacylamines which are acylating reagents and undergo further reactions depending upon the reaction conditions and nature of the other components. The reaction can be conducted either stepwise or in a single pot combining all four reagents. In the latter case, the one pot procedure is conducted without using any reagents but the four components described above.

Suitable amine components, carbonyl components and acid components are well known in the art. Likewise, isocyanides are either commercially available or can be prepared by conventional means well known in the art. For example, isocyanides can be prepared from primary amines by first forming the N-formyl amide therefrom and then dehydrating amide with thiophosgene in the presence of a tertiary amine (e.g., triethylamine) as shown in the reaction below:

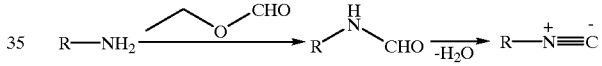

Examples of commercially available isocyanides include, for instance, t-butyl isocyanide, 1,13,3-tetramethylbutyl isocyanide, tosylmethyl isocyanide, cyclohexyl isocyanide, benzyl isocyanide, methyl isocyanoacetate, ethyl isocyanoacetate, t-butyl isocyanoacetate, hexyl isocyanide, i-propyl isocyanide, 2,6-dimethylphenyl isocyanide, trimethylsilylmethyl isocyanide, diethyl(isocyanomethyl) phosphonate, 2-(4-morpholinyl)-ethyl isocyanide, 1,6-diisocyanohexane.

If the amine component is selected to be cysteine or a cysteine analogue, the $R^1$ is hydrogen and $R^4$ is —$CHR^8R^9$. Likewise, if the carboxyl component is selected to be cysteine or a cysteine analogue, the $R^1$ is —$CHR^8R^9$ and $R^4$ is hydrogen.

Assay Conditions

The assay for collagenase-1 inhibition activity was performed using a HCBC buffer (pH 7.4, 20 mM Hepes (N-[2-hydroxyethyl]piperazine-N'-[2-ethanesulfonic acid], 5 mM $CaCl_2$, 0.02% Brij35, 0.5 mM cysteine) which was vacuum degassed for 20 minutes prior to addition of the cysteine. Collagenase-1 was added to the HCBC buffer at a concentration of 5 nM.

The compounds tested for collagenase-1 inhibitor activity was first diluted into 50% methanol (first degassed by bubbling argon on ice for at least 30 minutes) in HCBC and always kept on ice.

The substrate, Mca, was obtained from Bachem Bioscience Inc. as product number M1895 and is a peptide substrate for collagenase-1 having a fluorescent/quencher pair. In the intact peptide, the fluorescence is quenched by proximity of the quencher moiety to the fluorescence moiety. Upon digestion of this peptide by the collagenase-1, the quencher moiety is separated from the fluorescent moiety and, accordingly, collagenase activity can be determined by increases in fluorescence.

The substrate, 5 mM Mca in DMSO stock, was diluted into HCBC to 100 μM and then used in the assay as described below.

The assay was conducted by using multiple pipettes to add 172 μL of collagenase-1 to each well and 8 μL of candidate inhibitor compound in 50% methanol. The solution was then mixed and maintained for 3 minutes. At that time, 200 μL of 100 μM of the Mca solution described above was added to initiate the reaction.

The degree of enzyme activity, as compared to the controls without inhibitor compound, was measured over a 30 minute period at 1 minute intervals by measuring the slope of the fluorescence curve via conventional methods.

The compounds 1–8 of Table I above are all active in inhibiting collagenase-1 activity in this assay and each of these compounds had an $IC_{50}$ of less than 100 μM.

The assay for stromelysin-1 is conducted similarly. See, for example, U.S. patent application Ser. No. 08/549,346 filed Oct. 27, 1995 which application is incorporated herein by reference.

IV. Utility

A. Disease Indications

The invention also provides pharmaceutical compositions that include the collagenase-1 and/or stromelysin-1 metalloprotease inhibitors described herein. The pharmaceutical compositions comprise the compounds of the present invention in an amount effective to treat or control disease states associated with such metalloproteases in humans or other animals in need of such treatment. Such disease states involve, for example, tissue degradation and inflammatory conditions. Conditions treatable with the pharmaceutical compositions include, for example, osteoarthritis, rheumatoid arthritis, septic arthritis, articular cartilage degradation, tumor invasion in certain cancers, periodontal disease, dermatological conditions, bone resorption, arthropathy, corneal ulcerations, proteinuria, dystrophobic epidermolysis bullosa, coronary thrombosis associated with atherosclerotic plaque rupture, aneurysmal aortic disease, Crohn's disease, multiple sclerosis and the cachexia associated with cancer or human immunodeficiency virus infection. The collagenase-1 and stromelysin-1 metalloprotease inhibitors also promote wound healing. The present compounds are also designed to be effective birth control agents.

Pharmaceutical salts of the compounds of the present invention suitable for administration by a variety of routes are known in the art and need not be described herein in detail. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium, ammonium, and $NW_nH_m$ bases and salts wherein each of n and m are 0 to 4 and n+m is 4, and wherein W is a $(C_1-C_{18})$alkyl. Pharmaceutically acceptable salts of an amino group include, but are not limited to, salts of organic carboxylic acids such as acetic, lactic, tartaric, malic, isothionic, lactobionic and succinic acids; organic sulfonic acids such as methane-sulfonic, ethanesulfonic, benzenesulfonic and p-toluylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as sodium ($Na^+$), and $NW_nH_m$, wherein W is a $(C_1-C_8)$alkyl group, and n and m are 0 to 4, and n+m is 4.

The compounds of this invention can also be labeled by association with a detectable marker substance (e.g., radiolabeled with $^{125}I$) to provide reagents useful in detection and quantification of metalloproteinase inhibitors in solid tissue and fluid samples such as blood or urine.

B. Formulations

Also part of this invention is a pharmaceutical composition of matter comprising at least one compound of the invention described above, mixtures thereof, and/or pharmaceutical salts thereof; and a pharmaceutically-acceptable carrier therefore. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

Suitable carriers are well known in the art and vary with the desired form and mode of administration of the pharmaceutical composition. For example, they may include diluents or excipients such as fillers, binders, wetting agents, disintegrators, surface-active agents, lubricants and the like. Typically, the carrier may be a solid, liquid or vaporizable carrier, or combinations thereof. In one preferred embodiment, the composition is a therapeutic composition and the carrier is a pharmaceutically-acceptable carrier.

The compounds of the invention or salts thereof may be formulated together with the carrier into any desired unit dosage form. Typical unit dosage forms include tablets, pills, powders, solutions, suspensions, emulsions, granules, capsules, and suppositories.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous and intradermal) administration, with parenteral formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further comprise oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The compound of the invention may be present in the composition in a broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The invention also provides a method of treating or controlling disease states associated with collagenase-1 and/or stromelysin-1 (e.g., for inhibiting collagenase-1 and/or stromelysin-1 in patients afflicted with a disease state in which collagen tissue is broken down by collagenase-1 and/or stromelysin-1) in a patient comprising administering to a patient an effective amount of the composition of this invention comprising any of the compounds of the present invention, pharmaceutically-acceptable salts thereof, or mixtures thereof.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. These include agents that are effective for the treatment of disease states involving tissue breakdown or inflammatory conditions in humans. Examples include any of those known in the art, such as known drugs for the treatment of arthritis, such as adrenocortical steroids, apazone, aspirin-like drugs, azathioprine, diclofenas, diflunisal, etodolac, fenamates, indomethacin, methotrexate, nabumetone, phenylbutazone, piroxicam, propionic acid derivatives, such as ibuprofen, naproxen, fenoprofen, ketoprofen, and flurbiprofen, salicylates, sulindac, and tolmetin; PMN elastase inhibitors such as those described in European Patent Application 337 549, glucagon, dextrose, diazoxide, phenytoin, thiazide diuretics and somatostatin, among others.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained.

C. Mode of Administration

The mode of administration of the compounds of this invention depends on the disease to be treated and can be local administration (e.g., for ulceration or periodontal disease) or systemic administration (enteral or parenteral). The compound according to the invention, also referred to herein as the active ingredient, may be administered for therapy by any suitable routes, including oral, rectal, nasal, vaginal and parenteral (including intraperitoneal, subcutaneous, intramuscular, intravenous and intradermal) routes. For example, in the treatment of arthritis, the compounds can be administered orally, intravenously, subcutaneously or intramuscularly or, if appropriate, directly into the affected tissues by intraarticular injection. The compounds can be used in aqueous solution, or in the form of an ointment, gel or similar formulation for local applications or, if appropriate, in a pharmaceutical form which permits a slow release of the product, for example through encapsulation in an inert polymer.

It will be appreciated that the preferred route will vary with the condition and age of the patient, the nature of the disorder and the chosen active ingredient including other therapeutic agents. Preferred is the oral or intravenous route. However, other routes may also be utilized depending on the conditions of the patient and how long-lasting the treatment is.

The dosage of the compound of Formula I, pharmaceutically-acceptable salts or mixtures thereof, in the compositions of the invention administered to a patient will vary depending upon several factors, including, but not limited to, the age and weight of the patient, the type of disease state treated, how advanced the disease state is, the general health of the patient, the severity of the symptoms, whether the compound of Formula I is being administered alone or in combination with other therapies or other active ingredients, the incidence of side effects and the like.

In general, a dose suitable for application in the treatment of the above-mentioned conditions is about 0.001 to 100 mg/kg body weight/dose, preferably about 0.01 to 60 mg/kg body weight/dose, and still more preferably of about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered. The daily dose may be adjusted taking into account, for example, the above identified variety of parameters.

To achieve good plasma concentrations, the active compounds may be administered, for instance, by intravenous injection of an approximate 0.1 to 5% solution of the active ingredient, optionally in saline, or orally administered as a bolus.

In order to further illustrate the present invention and the advantages thereof, the following specific examples are given, it being understood that the same is intended only as illustrative and in nowise limitative.

In the examples below as well as elsewhere in this specification, all temperatures are in degrees Celcuis (° C.). Also, in the examples below as well as elsewhere in the specification, the following abbreviations are intended to have the meanings set forth below. If not defined, the abbreviation has its generally accepted meaning:

BOC=butyloxycarbonyl
Cha=cyclohexylalanine
DCM=dichloromethane
DIEA=diisopropylethylamine
DKP=diketopiperazine
DMF=dimethylformamide
DMFP-OTs=1,3-dimethyl-2-fluoropyridinium 4-toluenesulfonate
eq.=equivalents
Fmoc=9-fluroenylmethoxycarbonyl
g=gram
HPLC=high performance liquid chromatography
mg=milligram
mL=milliliter
mmol=millimol
N=normal TES=triethylsilane
TFA=trifluoroacetic acid
TMOF=trimethylorthoformate
Trt=trityl
μL=microliters

EXAMPLES

Example 1

Preparation of L-Cha-OMe

To a 0° C. solution of acetyl chloride (8 mL) in methanol (150 mL) was added L-cyclohexylalanine (L-Cha-OH, available from Novabiochem, 1 gram). The resulting solution was heated to reflux and stirred for 2 hours under argon. Concentration in vacuo yielded the desired hydrochloride salt as a white crystalline powder (1.20 g, 93%). The structure was confirmed by NMR.

The hydrochloride salt prepared above (529 mg) was dissolved in methylene chloride (150 mL). The solution was washed with 5% aqueous sodium bicarbonate (50 mL×2). The organic layer was dried over magnesium sulfate and concentrated to yield L-Cha-OMe as a colorless oil (364 mg, 82%).

Example 2

To a solution of L-Cha-OMe (364 mg, 1.96 mmol) in TMOF (15 mL) under argon was added cyclohexanecarboxaldehyde (1.12 mL, 9.82 mmol). After 15 minutes, a solution of NaBH$_3$CN (308 mg, 4.9 mmol) in TMOF (15 mL) was added. The reaction mixture was stirred for one hour and was then cooled to 0° C. To the cold solution was added 2% aqueous hydrochloric acid (200 mL). The mixture was washed with petroleum ether (4×40 mL). Concentration aqueous sodium hydroxide was added dropwise to the aqueous layer at 0° C. until the pH was greater than 11. The product was extracted with ether (300 mL), washed with 5% aqueous sodium bicarbonate, and saturated aqueous sodium chloride and dried over magnesium sulfate. The organic layer was concentrated to an oil and diluted with petroleum ether. A 4N solution of hydrochloric acid in dioxane (2 mL) was added. Removal of the solvents followed by dilution with petroleum ether gave a white precipitate which was collected by filtration. The product (430 mg, 72%) was identified by NMR and mass spectroscopy.

Example 3

To a solution of Boc-Cys(Trt)-OH (584 mg, available from NovaBiochem) in methylene chloride (4 mL) was added DIEA (657 μL). To the clear solution was added DMFP-OTs (374 mg, 1.26 mmol, available from Fluka) and the reaction was stirred for 10 minutes. To the reaction mixture was then added the HCl salt of N-cyclohexylmethyl-L-Cha-Ome from Example 2 above. The resulting material was stirred at room temperature overnight, diluted with ether, washed with 2% aqueous hydrochloric acid (2×25 mL), 5% aqueous sodium bicarbonate (2×25 mL), and brine, and dried over magnesium sulfate. Concentration yielded crude product as an oil. Flash column chromatography on silica gel (eluting with ethyl acetate/hexane 1:9) gave the final product as a white foam (160 mg, 35%) which was identified by NMR and mass spectroscopy.

Example 4

To a mixture of the acylation product prepared above (60 mg) and TES (5 eq.) in dichloromethane (5 mL) under argon was added TFA (1.25 mL). The reaction was stirred for 20 minutes and the solvent was removed under vacuum. Degassed methanol (15 mL) was added and the reaction was stirred for 1 hour. The reaction was concentrated and purified by flash chromatography on silica gel (eluting with 2.5% methanol in dichloromethane) to yield the product as a white powder (20 mg, 65%). The product was Ellman's reagent positive and was further identified by $^{13}$C and $^1$H NMR and by mass spectroscopy.

Example 5

Several different libraries of compounds of Formula I were prepared via combinatorial chemistry using solid phase synthesis wherein all compound variations of the different R groups described below have been prepared. The solid phase synthesis for each of these libraries is illustrated by the synthesis of (3S, 6S)-5-N-cyclohexylmethyl-6-cyclohexylmethyl-3-mercaptomethyl-2,5-piperazinedione on solid support.

Synthesis of (3S, 6S)-5-N-cyclohexylmethyl-6-cyclohexylmethyl-3-mercaptomethyl-2,5-piperazinedione A. Coupling Fmoc-Cha to TentaGel Resin To a solution of Fmoc-cyclohexylalanine (2.4 g, 6.0 mmol) and DIEA (3.1 mL, 18 mmol) in DCM (15 mL) was added 1,3-dimethyl-2-fluoropyridium 4-toluenesulfonate (1.8 g, 6 mmol) under argon at room temperature. The solution was shaken for 10 minutes and TentaGel-S-OH resin (4.0 g, 1.2 mmol) added under argon. After mixing for 12 hours, the resin was filtered, washed with DMF, methanol, tetrahydrofuran and ether and then dried in vacuo. The loading of the resin was determined by Fmoc-cleavage with 20% piperidine/DMF. Yield was determined to be about 90%.

B. Reductive Alkylation with Cyclohexylcarboxaldehyde

To 200 mg (54 μmol) of TGS-Cha-NH$_2$ were added TMOF (2 mL) and cyclohexane carboxaldehyde (65 μL, 0.54 mmol). The resin was mixed for 30 minutes and acetic acid (31 μL, 0.54 mmol) was added. If that step was performed on the automated machine, the acetic acid would be added in 0.5 mL tetrahydrofuran. Mixing was continued for another 10 minutes and sodium cyanoborohydride in tetrahydrofuran (1.0 M solution, 1.5 mL) was added. After 30 minutes of mixing, the supernatant was drained and the resin washed with methanol, DMF and ether.

C. Coupling of Boc-Cys(Trt)-OH

A solution of Boc-Cys(Trt)-OH (339 mg, 1.25 mmol) and DIEA (653 μL, 3.75 mmol) in 1.5 mL anhydrous DMF was added to TGS-Cha-NH(Cha) followed by a solution of HATU (475 mg, 1.25 mmol) in 1.5 mL DMF. The resin was mixed for 12 hours. The supernatant was then drained and the resin washed three times with DMF followed by three ether washes.

D. Boc-deprotection and DKP-formation

For the Boc-deprotection, 2.5 mL of a 95% TFA/TES solution were added to the dry resin and mixed for 30 minutes. The TFA solution was drained and the resin washed three times with ether. A degassed solution of 1% acetic acid in toluene was added and mixed for 12 hours. The toluene solution was collected, concentrated and purified by HPLC if necessary. The DKP was characterized by NMR and mass spectroscopy.

The resulting libraries are defined in Tables II–V below. In the library of Table II, $R^1$, $R^3$, $R^5$, $R^6$ and $R^7$ are all hydrogen. In Tables III, IV and V, $R^3$, $R^4$, $R^5$, $R^6$ and $R^7$ are all hydrogen. In all libraries, n is one. All possible combinations of compounds were prepared.

TABLE II

| $R^4$ | $R^2$ |
|---|---|
| —$C_7H_{15}$ | —$CH_2$-p-ethoxy-φ |
| —$CH_2CH(CH_2CH_3)_2$ | —$(CH_2)_2$φ |
| —$CH_2$-p-ethyl-φ | —$CH_2$-cyclohexyl |
| —$CH_2CH(CH_3)_2$ | —$CH_2$-2-thienyl |
| —$(CH_2)_4CH_3$ | 4-Boc-2-histidinyl |
| —$CH_2$-cyclohexyl | 1-naphthyl |
| —$CH_2CH_2CH_3$ | 2-napthyl |
| —$CH_2CH_2CH(CH_3)_2$ | —$CH_2$φ |
| —$CH_2CH=CH$-φ(trans) | —$CH_2CH_2CH_3$ |
| —$CH_2CH(CH_3)CH_2CH_2CH=C(CH_3)_2$ | —$CH_2$-p-methoxy-φ |
| —$(CH_2)_2CH(CH_3)CH_2CH_2CH=C(CH_3)_2$ | —$CH(OBn)CH_3$ |
| —$(CH_2)_2CH(CH_3)$-φ | —$(CH_2)_4NHAc$ |
| —$CH_2CH=CHN(CH_3)_2$ (trans) | —$CH_2$-p-benzyloxy-φ |
| —$CH_2CH=CH(CH_2)_3CH_3$ (trans) | —$CH_2$-3-pyridyl |
| —$CH_2CH=CHCH=CHCH_2CH_3$ (trans, trans) | —$CH_2C(O)NH_2$ |
| —$CH_2CH=C(CH_3)_2$ | —$CH_2CH_2C(O)NH_2$ |
| —$CH_2CH=CH(CH_2)_2CH=CH—CH_2CH_3$ (trans, cis) | —$CH_2$—O—$CH_2$-φ |
| —$(CH_2)_9CH_3$ | —$CH_2CH_2CH_2CH_2$- (proline side chain) |

TABLE III

| $R^1$ | $R^2$ |
|---|---|
| —$(CH_2)_6CH_3$ | —$CH_2$-p-hydroxy-φ |
| —$CH_2CH(CH_2CH_3)_2$ | —$(CH_2)_2$φ |
| —$CH_2CH_2C(CH_3)_3$ | —$CH_2$-cyclohexyl (L) |
| —$(CH_2)_3SCH_3$ | —$CH_2$-2-thienyl (L) |
| —$CH_2$-p-φ-φ | —$CH_2CH(CH_3)_2$ |
| —$CH_2$—CH(φ)$_2$ | —$(CH_2)_3CH_3$ |
| —$CH_2CH_2CH_2$-φ | —$CH_2$-cyclohexyl |
| —$CH_2$-p-ethyl-φ | —$CH_2CH_2CH_3$ |
| —$CH_2CH(CH_3)_2$ | —$CH_2$-φ (L) |
| —$(CH_2)_4CH_3$ | —$CH_2$-φ (D) |
| —$CH_2C(CH_3)_3$ | —$CH_2$-p-methoxy-φ |
| —$CH_2$-cyclohexyl | —$CH_2$-S(Tr) |
| —$CH_2CH_2OCH_3$ | —$CH_2SCH_2$-p-methoxy-φ |
| —$CH_2$-p-methoxy-φ | —$CH_2CH_2$—S—$CH_3$ |
| —$CH_2$-p-N,N-dimethyl-φ | —$CH_2$-3-pyridyl |
| —$CH_2$-2-napthyl | —$CH_2$-thienyl (D) |
| —$CH_2CH_2CH_3$ | $CH_2CH_2$—C(O)NH(Tr) |
| —$(CH_2)_2CH(CH_3)_2$ | —$CH_2CH_2COO$-t-Bu |
| —$(CH_2)_6CH_3$ | —$CH_2$-p-hydroxy-φ |
| —$CH_2CH(CH_2CH_3)_2$ | —$(CH_2)_2$φ |
| —$CH_2CH_2C(CH_3)_3$ | —$CH_2$-cyclohexyl (L) |
| —$(CH_2)_3SCH_3$ | —$CH_2$-2-thienyl (L) |
| —$CH_2$-p-φ-φ | —$CH_2CH(CH_3)_2$ |
| —$(CH_2)_3$φ | —$(CH_2)_3CH_3$ |
| —$CH_2$-p-ethyl-φ | —$CH_2$-φ |
| —$CH_2CH(CH_3)_2$ | —$CH_2$-p-methoxy-φ |
| —$(CH_2)_4CH_3$ | —$CH_2$—S(Tr) |
| —$CH_2$-cyclohexyl | —$CH_2SCH_2$-p-methoxy-φ |
| —$CH_2CH_2OCH_3$ | —$CH_2CH_2$—S—$CH_3$ |
| —$CH_2$-p-methoxy-φ | —$CH_2$-3-pyridyl |
| —$CH_2$-p-dimethyl-φ | —$CH_2SCH_2NHC(O)CH_3$ |
| —$CH_2$-2-napthyl | —$(CH_2)_4NHC(O)$-3-pyridyl |
| —$(CH_2)_2CH(CH_3)CH_2CH_2CH=C(CH_3)_2$ | —$CH_2OCH_2$-φ |
| —$CH_2CH_2CH(CH_3)2$ | —$CH_2CH_2OCH_2$-φ |
| —$CH_2CH=CH$-φ (trans) | $CH_2$-1-naphthyl |
| —$CH_2CH(CH_3)CH_2CH_2CH=C(CH_3)_2$ | —$CH_2$-3-indolyl |
| | —$CH_2$-2,6-dichloro-4-hydroxy-φ |
| | —$CH_2$-p-chloro-φ |
| | —$CH_2$-2-pyridyl |
| | —$(CH_2)_3NHC(=NH)NH_2$ |
| | —$CH_2$-histidyl |

TABLE III-continued

| $R^1$ | $R^2$ |
|---|---|
| | —$(CH_2)_4NHC(O)CH_3$ |
| | —$(CH_2)_2S(O)CH_3$ |
| | —$(CH_2)_2S(O)_2CH_3$ |
| | —$(CH_2)_4NH_2$ |
| | —$CH_2$-p-nitro-φ |
| | —$CH_2$-p-benzyloxy-φ |
| | —$CH_2$-p-fluoro-φ |
| | —$CH_2$-p-(φC(O))-φ |
| | —$(CH_2)_2CH_3$ |
| | —$CH_2OH$ |
| | —$CH_2C≡CH$ |
| | —$(CH_2)_5CH_3$ |

TABLE IV

| $R^1$ | $R^2$ |
|---|---|
| —$(CH_2)_2CH_3$ | —$CH_2$-p-hydroxy-φ |
| —$CH_2CH=CHN(CH_3)_2$ (trans) | —$(CH_2)_2$φ |
| —$(CH_2)_8CH_3$ | —$CH_2$cyclohexyl (L) |
| —$CH_2$-p-(4-pyrrolidyl)-φ | —$CH_2$-2-thienyl (L) |
| —$CH_2$-p-ethyoxy-φ | —$CH_2CH(CH_3)_2$ |
| —$CH_2$-(3-N,N-dimethylpropoxy)-φ | —$(CH_2)_3CH_3$ |
| —$CH_2$-p-(t-butoxy)-φ | —$CH_2$-φ |
| —$CH_2$-3-thiophenyl | —$CH_2$-p-methoxy-φ |
| —$CH_2CH_2$-O-$CH_2CH_2$-φ | —$CH_2$—S(Tr) |
| —$CH_2$-p-benzyloxy-φ | —$CH_2SCH_2$-p-methoxy-φ |
| —$CH_2$-3-pyridyl | —$CH_2CH_2$—S—$CH_3$ |
| —$CH_2$-4-pyridyl | —$CH_2$-3-pyridylφ |
| —$CH_2$-2-pyrrolyl | —$CH_2SCH_2NHC(O)CH_3$ |
| —$CH_2$-2-quinolinyl | —$(CH_2)_4NHC(O)$-3-pyridyl |
| —$CH_2CH=CH$-p-(N,N-dimethylamino)φ | —$CH_2OCH_2$-φ |
| —$CH_2$-p-(N,N-dimethylamino)φ | —$CH_2CH_2OCH_2$-φ |
| —$CH_2$-5-nitrothiophenyl | —$CH_2$-1-naphthyl |
| —$CH_2$-2-(n-methylpyrrolidinyl) | —$CH_2$-3-indolyl |
| | —$CH_2$-2,6-dichloro-4-hydroxy-φ |
| | —$CH_2$-p-chloro-φ |
| | —$CH_2$-2-pyridyl |
| | —$(CH_2)_3NHC(=NH)NH_2$ |
| | —$CH_2$-histidyl |
| | —$(CH_2)_4NHC(O)CH_3$ |
| | —$(CH_2)_2S(O)CH_3$ |
| | —$(CH_2)_2S(O)_2CH_3$ |
| | —$(CH_2)_4NH_2$ |
| | —$CH_2$-p-nitro-φ |
| | —$CH_2$-p-benzyloxy-φ |
| | —$CH_2$-p-fluoro-φ |
| | —$CH_2$-p-(φC(O))-φ |
| | —$(CH_2)_2CH_3$ |
| | —$CH_2OH$ |
| | —$CH_2C≡CH$ |
| | —$(CH_2)_5CH_3$ |
| | —$CH_2$-2-(4-benyzl)-histidyl |

Example 6

Following the procedures set forth above, the following compounds have been prepared.

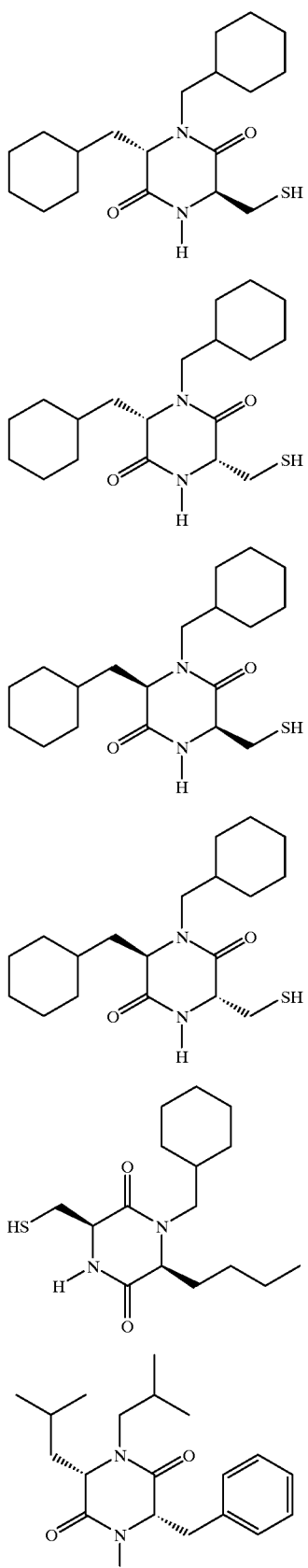

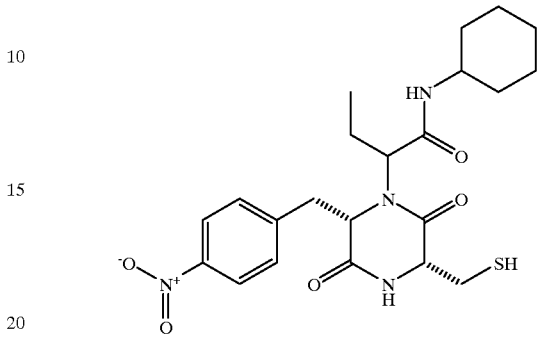

Example 7

This example illustrates the solid phase synthesis of diketopiperazine compounds using the Ugi reaction procedure well documented in the literature for the solution phase. Specifically, in this example, the following compound was prepared after decoupling from the resin.

A. Coupling of FmocPhe(p-NO$_2$)OH to TentaGel resin (TGS).

FmocPhe(p-NO$_2$)OH was coupled to TentaGel resin in the manner described above in Example 5A for FmocCha.

B. Solid Phase Ugi Reaction

To 200 mg (44 μmol) of TGS-Phe(p-NO$_2$)-NH$_2$ were added TMOF (1.5 mL) and propionaldehyde (32 μL, 0.44 mmol). The resin was mixed for about 20 minutes. A solution of BocCys(Trt)-OH (204 mg, 0.44 mmol) in methanol and cyclohexylisocyanide (56 μL, 0.44 mmol) were added. Mixing was continued for about 2 hours. The supernatant is then drained and the resin washed with DMF, ethanol and ether.

C. Boc-Deprotection and DKP-formation.

For the Boc-deprotection, 2.5 mL of a 95% TFA/TES solution were added to the dry resin and mixed for 30 minutes. The TFA solution was drained and the resin washed three times with ether. A degassed solution of 1% acetic acid in toluene was added and mixed for about 12 hours. The toluene solution was collected, concentrated and purified by HPLC yielding 9 mg (44% overall) of a colorless crystalline material. The product was characterized by NMR and mass spectroscopy and confirmed as the compound described above.

Following the procedure set forth in this example, the following additional compound was prepared merely by substitution of the appropriate starting materials:

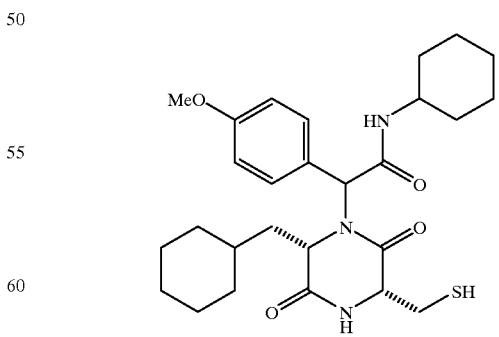

Both of the compounds described in Example 7 above have an IC$_{50}$ as described above of less than about 2 μM.

Other embodiments of the invention will be apparent to those skilled in the art from consideration of the specifica-

What is claimed is:

1. A compound of formula:

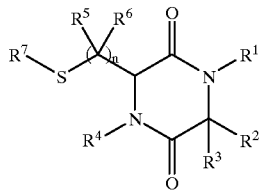

wherein $R^1$ is selected from the group consisting of —$CH_2R^8$ and —$CHR^8R^9$, and $R^4$ is selected from the group consisting of hydrogen and —$CH_2R^8$ and —$CHR^8R^9$;

$R^2$, $R^3$, $R^5$, $R^6$ and $R^8$ are independently selected from the group consisting of
(i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, and —$SO_2NH_2$, and X is selected from the group consisting of a bond, O, and NR' where R' is as defined above;
(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, and —$SO_2NH_2$, and Y is selected from the group consisting of a bond and NR' where R' is as defined above;
(v) alkenyl groups of from 2 to 10 carbon atoms;
(vi) alkynyl groups of from 3 to 10 carbon atoms;
(vii) carboxyl groups;
(viii) carboxyl ester groups wherein the ester group comprises from 1 to 12 carbon atoms;
(ix) heterocycles, either saturated, unsaturated or aromatic, having from 2 to 6 carbon atoms and 1 to 3 ring hetero atoms selected from the group consisting of nitrogen, oxygen and sulfur, optionally substituted;
(x) R—C(O)— groups where R is hydrogen or an alkyl group of from 1 to 12 carbon atoms, optionally substituted on the alkyl group;
(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —$SO_3$, and —$SO_2NH_2$; and
(xii) arylalkyl, optionally substituted on the aryl group and/or the alkyl group; or wherein $R^2$, $R^3$ and the carbon to which they are attached form a cycloalkyl or heterocyclic group; or $R^1$ and $R^2$ and the carbon and nitrogen to which they are attached, respectively, form a heterocyclic group;

$R^4$ and $R^5$ and the carbon and nitrogen to which they are attached, respectively, form a heterocyclic group;

$R^7$ is hydrogen;

$R^9$ is hydrogen, alkyl, substituted alkyl, aryl, substituted aryl, heterocyclic or substituted heterocyclic; and n is an integer from 1 to 3;

and a pharmaceutical salt thereof.

2. The compound of claim 1, wherein $R^8$, $R^5$, and $R^6$ are independently selected from the group consisting of hydrogen and lower alkyl.

3. The compound of claim 2, wherein $R^8$ is alkyl.

4. The compound of claim 2, wherein $R^2$ is alkyl.

5. The compound of claim 2, wherein both $R^8$ and $R^2$ are alkyl.

6. The compound of claim 5, wherein $R^1$ is —$(CH_2)_p$—$(C_6H_{11})$ and $R^2$ is —$(CH_2)_q$—$(C_6H_{11})$ wherein p and q are independently integers from one to five and $C_6H_{11}$ is cyclohexyl.

7. The compound of claim 6, wherein p and q are independently integers from one to three.

8. The compound of claim 7, wherein p is 1 and q is 1.

9. The compound according to claim 1 wherein $R^2$ is arylalkyl or substituted arylalkyl.

10. The compound according to claim 9 wherein the arylalkyl and substituted arylalkyl groups are represented by the formula —$CH_2$—$C_6H_4Z$ where Z is selected from the group consisting of hydrogen, hydroxy, alkyl, substituted alkyl, alkoxy, substituted alkoxy, amido, amino, aryloxy, carboxyl, halo, mercapto, cyano, nitro, —$SO_3$, —$SO_2NH_2$ at any location on the phenyl (—$C_6H_4$ ring).

11. The compound according to claim 1 wherein $R^4$ is hydrogen and $R^1$ is —$CHR^8R^9$ where $R^8$ is —$C(O)N(R')_2$ where each R' is independently selected from hydrogen, alkyl, substituted alkyl, aryl, substituted aryl, arylalkyl, substituted arylalkyl, heterocyclic and substituted heterocyclic and $R^9$ is as defined above.

12. The compound according to claim 1 wherein $R^1$ is hydrogen and $R^4$ is —$CHR^8R^9$ where $R^8$ is —$C(O)N(R')_2$ where each R' is independently selected from hydrogen, alkyl, substituted alkyl, aryl, substituted aryl, arylalkyl, substituted arylalkyl, heterocyclic and substituted heterocyclic and $R^9$ is as defined above.

13. A pharmaceutical composition comprising the compound of claim 1 in an amount effective for disease states associated with collagenase-1 and/or stromelysin-1 in patients in need of such treatment; and a pharmaceutically acceptable carrier.

14. A method for treating a patient suffering from rheumatoid arthritis, said method comprising administering to said patient an effective amount of a compound of the formula

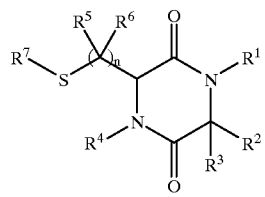

wherein:

R¹ and R⁴ are independently selected from the group consisting of hydrogen and —CH₂R⁸ and —CHR⁸R⁹;

R², R³, R⁵, R⁶ and R⁸ are independently selected from the group consisting of
(i) hydrogen;
(ii) an alkyl group of from 1 to 12 carbon atoms, optionally substituted;
(iii) —NR'C(O)—X—R" where R' and R" are independently selected from the group consisting of hydrogen, alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —SO₃, and —SO₂NH₂, and X is selected from the group consisting of a bond, O, and NR' where R' is as defined above;
(iv) —OC(O)Y—R" where R" is selected from the group consisting of alkyl of from 1 to 12 carbon atoms, substituted alkyl of from 1 to 12 carbon atoms, aryl groups of from 6 to 10 carbon atoms optionally substituted with from 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —SO₃, and —SO₂NH₂, and Y is selected from the group consisting of a bond and NR' where R' is as defined above;
(v) alkenyl groups of from 2 to 10 carbon atoms;
(vi) alkynyl groups of from 3 to 10 carbon atoms;
(vii) carboxyl groups;
(viii) carboxyl ester groups wherein the ester group comprises from 1 to 12 carbon atoms;
(ix) heterocycles, either saturated, unsaturated or aromatic, having from 2 to 6 carbon atoms and 1 to 3 ring hetero atoms selected from the group consisting of nitrogen, oxygen and sulfur, optionally substituted;
(x) R—C(O)— groups where R is hydrogen or an alkyl group of from 1 to 12 carbon atoms, optionally substituted on the alkyl group;
(xi) aryl group of from 6 to 10 carbon atoms optionally substituted with 1 to 3 substituents on the aryl moiety selected from the group consisting of hydroxy, alkyl, substituted alkyl, alkoxy, substituted alkoxy, amido, amino, aryloxy, carboxyl, halo, mercapto, cyano, nitro, —SO₃, and —SO₂NH₂; and
(xii) arylalkyl, optionally substituted on the aryl group and/or the alkyl group;

or wherein R², R³ and the carbon to which they are attached form a cycloalkyl or heterocyclic group; or R¹ and R² and the carbon and nitrogen to which they are attached, respectively, form a heterocyclic group;

R⁴ and R⁵ and the carbon and nitrogen to which they are attached, respectively, form a heterocyclic group;

R⁷ is hydrogen and alkyl of from 1 to 12 carbon atoms, R⁸C(O)— and R⁸S— where R⁸ is as defined above;

R⁹ is hydrogen, alkyl, substituted alkyl, aryl, substituted aryl, heterocyclic or substituted heterocyclic; and n is an integer from 1 to 3;

or a pharmaceutical salt thereof.

\* \* \* \* \*